(12) United States Patent
Dekker et al.

(10) Patent No.: US 9,822,352 B2
(45) Date of Patent: *Nov. 21, 2017

(54) CHYMOSINE ENZYME VARIANTS

(71) Applicant: DSM IP ASSETS B.V., Heerlen (NL)

(72) Inventors: Petrus Jacobus Theodorus Dekker, Echt (NL); Rene Marcel De Jong, Echt (NL); Cornelis Marinus Muijlwijk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 302 days.

This patent is subject to a terminal disclaimer.

(21) Appl. No.: 14/397,866

(22) PCT Filed: May 3, 2013

(86) PCT No.: PCT/EP2013/059315
§ 371 (c)(1),
(2) Date: Oct. 30, 2014

(87) PCT Pub. No.: WO2013/164479
PCT Pub. Date: Nov. 7, 2013

(65) Prior Publication Data
US 2015/0118356 A1    Apr. 30, 2015

Related U.S. Application Data

(60) Provisional application No. 61/642,095, filed on May 3, 2012, provisional application No. 61/745,063, filed on Dec. 21, 2012.

(30) Foreign Application Priority Data

May 3, 2012    (EP) .................................... 12166673
Dec. 21, 2012  (EP) .................................... 12199178
Dec. 21, 2012  (EP) .................................... 12199277

(51) Int. Cl.
*C12N 9/64*    (2006.01)
*A23C 19/032*  (2006.01)
*A23C 19/068*  (2006.01)
*A23C 19/072*  (2006.01)

(52) U.S. Cl.
CPC .......... *C12N 9/6483* (2013.01); *A23C 19/032* (2013.01); *A23C 19/0326* (2013.01); *A23C 19/0684* (2013.01); *A23C 19/072* (2013.01); *C12Y 304/23004* (2013.01); *A23C 2220/202* (2013.01); *A23C 2250/15* (2013.01)

(58) Field of Classification Search
CPC .......... C12Y 304/23004; C12N 9/6483; A23C 19/0326; A23C 19/032; A23C 19/072; A23C 2220/202; A23C 2250/15; A23C 19/0684
See application file for complete search history.

(56) References Cited

FOREIGN PATENT DOCUMENTS

WO    0236752 A2      5/2002
WO    2008098973 A1   8/2008

OTHER PUBLICATIONS

Branden et al., Introduction to Protein Structure, Garland Publishing Inc., New York, p. 247.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
International Search Report from corresponding PCT/EP2013/059315, dated Oct. 30, 2013.
Suzuki et al., "Alteration of catalytic properties of chymosin by site-directed mutagenesis", XP000009488, Protein Engineering, vol. 2, No. 7, pp. 563-569, May 1, 1989, Eynsham, Oxford, GB.
Suzuki et al., Site-directed mutagensis reveals functional contribution of Thr218, Lys220 and Asp304 in chymosin, Department of Agriculture Chemistry, Faculty of Agriculture, The University of Tokyo, Tokyo, Japan, Protein Engineering, vol. 4, No. 1, pp. 69-71, 1990.
Chitpinityol et al., "Chymosin and aspartic proteinases", XP-002685254, Food Chemistry, vol. 61, No. 4, pp. 395-418, 1998.
Chitpinityol et al., "Site-specific mutations of calf chymosin B which influence milk-clotting activity", XP-002685255, Food Chemistry, vol. 62, No. 2, pp. 133-139, Jun. 1998.
Palmer et al., "Bovine Chymosin: A Computational Study of Recognition and Binding of Bovine k-Casein", XP-002685251, Biochemistry, Mar. 2010, vol. 49, No. 11, pp. 2563-2573.
Rao et al, "Molecular and Biotechnological Aspects of Microbial Proteases", XP-002685252, Microbiology and Molecular Biology Reviews, Sep. 1998, p. 597-635, vol. 62, No. 3, Division of Biochemical Sciences, National Chemical Laboratory, Pune, India.
Gilliland et al., "The Three-Dimensional Structure of Recombinant Bovine Chymosin at 2.3 A Resolution", XP-002685253, Proteins: Structure, Function, and Genetics 8:82-10 (1990), pp. 83-101.
Houen et al., "The Primary Structure and Enzymic Properties of Porcine Prochymosin and Chymosin", XP002901712, Int. J. Biochem. Cell Biol. vol. 28, No. 6, pp. 667-675, Jan. 1, 1996, Pergamon, GB.

(Continued)

*Primary Examiner* — Delia Ramirez
(74) *Attorney, Agent, or Firm* — McBee Moore Woodward & Vanik IP, LLC; Susan McBee; Chester Moore

(57) ABSTRACT

A variant polypeptide having chymosin activity, wherein the variant has an amino acid sequence which, when aligned with the chymosin comprising the sequence set out in SEQ ID NO: 2, comprises at least one substitution of an amino acid residue corresponding to any of amino acids 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295
said positions being defined with reference to SEQ ID NO: 2 and wherein the variant has one or more altered properties as compared with a reference polypeptide having chymosin activity. Such a variant polypeptide may be used in the preparation of a cheese.

17 Claims, 1 Drawing Sheet

(56) References Cited

OTHER PUBLICATIONS

Kappeler, "Characterization of recombinant camel chymosin reveals superior properties for the coagulation of bovine and camel milk", Elsevier, XP024923721, Biochemical and Biophysical Research Communications 342:2 (Apr. 7, 2006), pp. 647-654.
Kieliszewski M. "Protein production; protein secretion; expression; Chymosin; BOND_PC; chymosin", Jun. 26, 2008, ARK01109.
Bansal, N. et al., "Suitability of recombinant camel (*Camelus dromedarius*) chymosin as a coagulant for Cheddar cheese", International Dairy Journal, vol. 19, 2009, pp. 510-517.

* cited by examiner

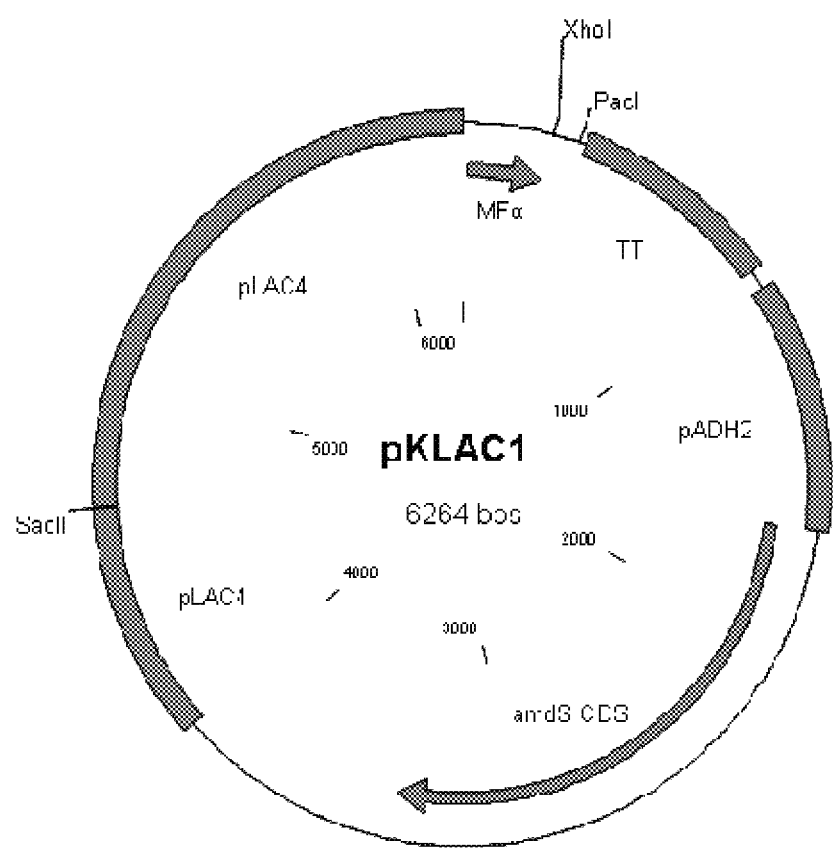

CHYMOSINE ENZYME VARIANTS

CROSS REFERENCE TO RELATED APPLICATIONS

This application is a §371 National Stage Application of PCT/EP2013/059315, filed May 3, 2013, which claims priority to EP 12155573.9, filed May 3, 2012, to U.S. 61/642,095, filed May 3, 2012, to EP 12199178.0, filed Dec. 21, 2012, to EP 12199277.0, filed Dec. 21, 2012, and to U.S. 61/745,063, filed Dec. 21, 2012.

BACKGROUND

Field of the Invention

The invention relates to a variant polypeptide having chymosin activity. The invention also relates to a nucleic acid sequence encoding such a variant, to a recombinant expression vector a said nucleic acid construct and to a recombinant host cell comprising a said expression vector. Further, the invention relates to a method for producing a chymosin via use of such a host cell. Also, the invention relates to a method of producing a chymosin polypeptide variant. The invention further relates to a composition comprising a chymosin variant, to use of such a chymosin variant or chymosin variant-containing composition in the preparation of a cheese, to a process for the production of a cheese and to the resulting cheese.

Description of Related Art

Enzymatic coagulation of milk by milk clotting enzymes, such as chymosin and pepsin, is one of the most important processes in the manufacture of cheeses. Enzymatic milk coagulation is a two-phase process: a first phase where a proteolytic enzyme, chymosin or pepsin, attacks kappa-casein, resulting in a metastable state of the casein micelle structure and a second phase, where the milk subsequently coagulates and forms a coagulum. Chymosin (group 3.4.23.4 according to the Enzyme Nomenclature, 1992 of the International Union of Biochemistry and Molecular Biology, IUBMB) and pepsin (EC 3.4.23.1), the milk clotting enzymes of the mammalian stomach, are aspartic proteases belonging to a broad class of peptidases. Aspartic proteases are found in eukaryotes, retroviruses and some plant viruses.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, ie Bos taurus, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprising 323 aa is a mixture of two forms, A and B, both of which are active, and sequencing data indicate that the only difference between those two forms is an aspartate residue at position 290 in chymosin A and a glycine residue at that position in chymosin B.

However, it is evident that the productivity in terms of overall yield of gene product is an important factor for the cost effectiveness of industrial production of the enzyme. Improvement of the productivity of chymosin would lead to a lower production costs and reduced use of resources. Accordingly, a continued industrial need exists to improve the productivity of chymosin in recombinant expression systems.

Additionally, there is a need for a chymosin with modified proteolytic activity under cheese-making conditions. In most cheeses, chymosin is responsible for "primary" proteolysis, which leads to the release of peptides that are later used by lactic acid bacteria for "secondary" proteolysis and flavour formation during ripening.

SUMMARY

The invention relates to variant polypeptides having chymosin activity, i.e. to chymosin variants. A chymosin variant of the invention may have one or more improved properties in comparison with a reference polypeptide, the reference polypeptide typically having chymosin activity. A reference polypeptide may be a wild-type chymosin, such as wild-type chymosin, for example from a bovine species such as Bos taurus. Variant polypeptides of the invention may be referred to as a "chymosin variant", an "improved chymosin" and the like.

The improved property will typically be a property with relevance to the use of the variant chymosin in the preparation of a cheese. A chymosin variant with an improved property relevant for cheese making may demonstrate:
  Increased productivity, for example measured in IMCU per liter fermentation broth;
  Increased specific activity, for example measured in IMCU per mg chymosin protein;
  Increased or decreased specificity at the pH relevant in cheese making and ripening, wherein specificity may, for example, be measured by dividing the clotting activity by the proteolytic activity (C/P);
  Increased or decreased activity at low temperature;
  Increased or decreased targeting of the chymosin enzyme to the cheese curd
  Decreased temperature stability;
  Increased clotting activity at low pH, decreased proteolytic activity at low pH or decreased proteolytic activity at low temperature;
  Decreased salt stability or decreased activity at high salt concentration; and/or
  Increased or decreased ripening of the cheese produced with variant chymosin.

Each of these improvements may be determined as compared with a reference polypeptide.

In particular, a variant chymosin of the invention may show improved productivity in comparison with a reference polypeptide. Alternatively, or in addition, a variant chyomsin of the invention may show modified proteolytic activity in a cheese matrix as compared with a reference polypeptide. The variant may show reduced or increased proteolytic activity as compared with a parent polypeptide. Alternatively, or in addition, a variant chymosin of the invention may show an altered, such as reduced, temperature stability or an altered activity at pH relevant for the cheese making process, such as a low pH, as compared with a reference polypeptide.

According to the invention, there is thus provided a variant polypeptide having chymosin activity, wherein the variant has an amino acid sequence which, when aligned with the chymosin comprising the sequence set out in SEQ ID NO: 2, comprises at least one substitution of an amino acid residue corresponding to any of amino acids 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 said positions being defined with reference to SEQ ID NO: 2 and wherein the variant has one or more altered properties as compared with a reference polypeptide having chymosin activity.

The invention also provides:
- a nucleic acid sequence encoding a variant of the invention;
- a nucleic acid construct comprising such a nucleic acid sequence operably linked to one or more control sequences capable of directing the expression of a chymosin in a suitable expression host;
- a recombinant expression vector comprising such a nucleic acid construct; and
- a recombinant host cell comprising such an expression vector.

The invention also relate to a method for producing a chymosin comprising cultivating the host cell of the invention under conditions conducive to production of the chymosin and recovering the chymosin.

Also, the invention relates to a method of producing a chymosin polypeptide variant, which method comprises:
a) selecting a polypeptide having chymosin activity;
b) substituting at least one amino acid residue corresponding to any of amino acids 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 said positions being defined with reference to SEQ ID NO: 2;
c) optionally substituting one or more further amino acids as defined in b);
d) preparing the variant resulting from steps a)-c);
e) determining a property of the variant; and
f) selecting a variant having an altered property in comparison to the chymosin comprising the sequence set out in SEQ ID NO: 2, thereby to produce an chymosin polypeptide variant.

Further the invention relates to:
- a composition comprising the variant of the invention or obtainable by a method of the invention;
- use of a variant chymosin according to the invention or of a composition of the invention in the preparation of a cheese;
- a process for the production of a cheese, which method comprises comprising adding a milk clotting effective amount of a variant chymosin according to the invention or of a composition of the invention to milk and carrying out appropriate further cheese manufacturing steps; and
- a cheese obtainable by such process or use.

BRIEF DESCRIPTION OF THE DRAWINGS

FIG. 1 sets out a diagrammatic representation of pKLAC1, the plasmid used for production of chymosin variants.

DESCRIPTION OF THE SEQUENCE LISTING

SEQ ID NO: 1 sets out the nucleic acid sequence of the wild type pro-chymosin B gene sequence from *Bos taurus* with codon adaptation for expression in *K. lactis* and with linkers to allow cloning into pKLAC1.

SEQ ID NO: 2 sets out the amino acid sequence of the mature chymosin B sequence from *Bos taurus*.

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Herein, "chymosin" typically indicates an aspartic protease, group 3.4.23.4 according to the Enzyme Nomenclature, 1992 of the International Union of Biochemistry and Molecular Biology, IUBMB. Chymosin is naturally produced by gastric chief cells in juvenile mammals. Chymosin is the main enzymatic component in rennet. Calf rennet is obtained of the lining of the abomasum (the fourth and final, chamber of the stomach) of young, unweaned calves.

Prochymosin is in the present context to be understood as the precursor or proenzyme of chymosin. Prochymosin appears to possess a leader sequence (pro-part) on the N-terminal side of chymosin and said leader sequence is believed to be cleaved off during activation of the prochymosin. Furthermore in this context, preprochymosin consists of prochymosin to which is added on the N-terminal end of prochymosin a hydrophobic leader sequence. This leader sequence, also called secretion signal or prepart, is cleaved off when the protein is secreted. Chymosin is in the cell initially synthesised as preprochymosin (Harris et al., Nucleic acid Research 1982, Apr. 10, 2177-2187 Molecular cloning and nucleotide sequence of cDNA coding for calf preprochymosin).

A gene or cDNA coding for chymosin or pro-chymosin, for example a variant of the invention, may be cloned and over-expressed in a host organism. Well known host organisms that have been used for chymosin over-expression in the past include *Aspergillus, Kluyveromyces, Trichoderma, Escherichia coli, Pichia, Saccharomyces, Yarrowia, Neurospora* or *Bacillus*.

Currently, bovine chymosin is manufactured industrially using recombinant DNA technology, e.g. using filamentous fungi such as *Aspergillus* species, yeast strains, e.g. of *Klyuveromyces* species, or bacterial species, e.g. *E. coli*, as host organisms. Such recombinant microbial production strains are constructed and continuously improved using DNA technology as well as classical strain improvement measures directed towards optimising the expression and secretion of a heterologous protein.

In the invention, a chymosin variant may be provided in the form of pre-prochymosin, prochymosin or (mature) chymosin. A corresponding nucleic acid sequence may also be provided, i.e. a polynucleotide that encodes a pre-prochymosin, prochymosin or (mature) chymosin is provided.

Herein, positions which may be substituted to achieve a variant of the invention are defined with reference to SEQ ID NO: 2 which is the mature bovine chymosin, i.e. it is a sequence which does not include a prepro or pro sequence.

The invention concerns variant polypeptides having chymosin activity as compared with a reference polypeptide having chymosin activity. The reference polypeptide may typically be a wild-type polypeptide having chymosin activity, such as the chymosin of SEQ ID NO: 2 or a related sequence. The reference polypeptide may also be referred to as a parent polypeptide or comparison polypeptide.

More concretely, the invention relates to a variant polypeptide having chymosin activity, wherein the variant has an amino acid sequence which, when aligned with the chymosin comprising the sequence set out in SEQ ID NO: 2, comprises at least one substitution of an amino acid residue corresponding to any of amino acids 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 said positions being defined with reference to SEQ ID NO: 2 and wherein the variant has one or more altered properties as compared with a reference polypeptide having chymosin activity.

A wild type reference polypeptide may be obtained from any suitable organisms. Typically, a wild type reference polypeptide may be obtained from a mammal, preferably one in which pre-prochymosin is produced naturally in the gastrointestinal tract.

Such mammals include bovine species, i.e. species from the family Bovinae, for example *Bos taurus*, buffalo species, including water buffaloes, Indian buffalo and Cape buffaloes. A reference polypeptide may be an ovine or caprine wild type sequence. A reference polypeptide may be a wild type sequence from a Camelidae species, for example from the genus *Camelus* including the two species *Camelus dromedarius* and *Camelus bactrianus*, the genus *Lama* including *Lama glama, Lama guanicoe* and *Lama paco* or the genus *Vicuna*.

Preferably, the reference polypeptide is the chymosin set out in SEQ ID NO: 2.

A variant polypeptide will typically have an improved property as compared to a reference polypeptide, in particular with respect to a property relevant to the use of the variant polypeptide in cheese making.

In particular, the improved property may relate to proteolytic activity and/or to productivity.

Improved productivity may be demonstrated by a chymosin variant that shows improved expression as compared with a parent polypeptide. Alternatively, or in addition, increased productivity of a variant chymosin may be demonstrated by a chymosin with a higher specific activity as compared with a parent polypeptide.

Thus, one objective of the present invention is to provide a method of producing a nonbovine pre-prochymosin, prochymosin or chymosin recombinantly at a high yield. The invention relates to variant chymosins that, when expressed in the same host cell and under essentially identical conditions, is expressed at activity yields which are significantly higher than are the obtained activity yields of a reference chymosin, such as that of SEQ ID NO: 2.

In accordance herewith, the above method of the invention is preferably a method wherein the yield of non-bovine pre-prochymosin, prochymosin or chymosin milk clotting activity is at least 10%, 25%, 50%, 100% or 200% higher than the yield of bovine pre-prochymosin, prochymosin or chymosin milk clotting activity obtained when using, under identical production conditions, the same expression vector, but with a coding sequence for bovine pre-prochymosin, prochymosin or chymosin in place of the sequence coding for the non-bovine pre-prochymosin, prochymosin or chymosin.

A variant chymosin of the invention may have modified, in particular reduced, proteolytic activity in a cheese matrix as compared with a parent polypeptide. Such an improved chymosin may have an increased specificity, for example, at the pH of cheese ripening. The specificity of a chymosin preparation can be measured, in particular, by determination of the C/P ratio. A higher C/P ratio implies a higher specificity which may lead to a reduced primary proteolysis.

Alternatively, or in addition, a variant chymosin of the invention with a reduced proteolytic activity in a cheese matrix may show reduced curd targeting in comparison with a parent polypeptide. Reduced curd targeting will result in less inclusion of chymosin in the cheese matrix and hence reduced primary proteolysis.

Alternatively, or in addition, a variant chymosin of the invention with a reduced proteolytic activity in a cheese matrix may have a reduced temperature stability in comparison with a parent polypeptide. Some cheese types are produced with a cooking or stretching step where the curd is heated before forming the final cheese. During such a heating step chymosin with a reduced temperature stability will be inactivated and hence reduced proteolysis in the cheese matrix will occur.

Alternatively, or in addition, a chymosin with a reduced proteolytic activity in a cheese matrix may have a reduced activity at lower temperatures in comparison with a parent polypeptide. Many cheeses are stored and ripened (cured) at decreased temperatures. A chymosin with decreased proteolytic activity at lower temperature will lead to a reduced proteolysis in the cheese matrix.

Another way to obtain a chymosin with a reduced proteolytic activity in a cheese matrix is to engineer chymosin variants that have reduced salt stability or reduced activity when salt concentration is increased. Many cheese types are salted by brining or mixing the salt through the curd grains. On average the salt concentration in cheese ranges from 0.8% (cottage cheese) to 3% (feta and blue cheese). Consequently, a chymosin with a reduced salt stability or a reduced activity under these conditions will lead to a cheese with reduced proteolysis.

A chymosin with a decreased proteolytic activity in the cheese will result in less softening and ripening of the cheese, which may be advantageous for young cheeses, such as Mozzarella, pizza cheese and pasta filata types, by increasing shelf life and improving slicing and shredding due to the harder structure. Decreased primary proteolysis also implies that the development of bitter taste in the cheese during maturation is reduced. This may be especially relevant in cheeses with a higher water content where primary proteolysis is increased and bitterness is perceived as a problem.

Additionally, a chymosin with a decreased proteolytic activity during cheese making may lead to reduced casein loss in the whey and therefore an increased cheese yield. Also the value of the whey may increase when a chymosin with decreased proteolytic activity is used.

Accordingly, a variant chymosin of the invention may be particular suitable in such applications.

In contrast, a variant of the invention may demonstrate increased primary proteolysis in the cheese matrix. An increased primary proteolysis generally implies that development of flavour in the cheese during maturation is increased. Ripening time of semi-hard and hard cheeses may be reduced by using such chymosin variants thereby lowering production costs and limiting spoilage problems. Additionally, increased primary proteolysis may lead to a faster fusion of curd grains during the first weeks of storage, reducing the time needed before a cheese can be cut or shredded.

A low primary proteolysis is especially found in cheeses made with ultra-filtrated milk where the casein concentration during renneting is higher and less chymosin is dosed. Therefore, cheese made with ultra-filtrated milk often show defects in ripening. A chymosin with increased activity in the cheese matrix may compensate for the decreased dosage required during renneting. Also a higher pH of whey at draining and lower cook temperatures, normally employed in low-fat cheese manufacture, lead to a lower retention of chymosin in cheese. This is partly the reason for a lower extent of primary proteolysis during ripening and the firm structure of low-fat cheeses. Also here, a chymosin with increased activity in the cheese matrix may be useful in repairing structural defects in low-fat cheese. Accordingly, a chymosin of the invention showing increased proteolysis may be used in such applications.

There may be several ways to obtain a chymosin with an increased proteolytic activity in a cheese matrix. One way to obtain such an improved chymosin is to select for chymosin variants that have a decreased specificity at the pH of cheese ripening. The specificity of a chymosin preparation can be measured by determination of the C/P ratio. A lower C/P ratio implies a lower specificity which may lead to an increased primary proteolysis.

Another way to obtain a chymosin with an increased proteolytic activity in a cheese matrix is to select for chymosin variants that have an increased curd targeting. Increased curd targeting will result in more inclusion of chymosin in the cheese matrix and hence increased primary proteolysis.

Another way to obtain a chymosin with an increased proteolytic activity in a cheese matrix is to select for chymosin variants that have a high activity at the lower temperature used for cheese ripening. Such chymosin variants may increase the primary proteolysis in the cheese matrix.

Herein, the term "IMCU" is understood International Milk Clotting Units. One IMCU equals about 0.126 nmol of bovine chymosin B (e.g. Maxiren or CHY-MAX). The strength of a milk clotting enzyme (such as chymosin enzyme present in a composition of the present invention) is determined as the milk clotting activity (IMCU per ml or per gram). Following the addition of diluted coagulant to a standard milk substrate, the milk will flocculate. The milk clotting time is the time period from addition of the coagulant until formation of visible flocks or flakes in the milk substrate. The strength of a coagulant sample is found by comparing the milk clotting time for the sample to that of a reference standard, a normal. This is expressed in IDF standard 157A:1997 which gives the IMCU definition: The total milk-clotting activity of the first batch of calf chymosin reference standard powder has once and for all been set at 1000 International Milk-Clotting Units per gram (IMCU/g). Further preparations of reference standards will be set relative to the previous reference. IMCU principle: Determination of the time needed for visible flocculation of renneted standard milk substrate with 0.05% calcium chloride, pH6.5. IMCU/ml of a sample is determined by comparison of the clotting time to that of a standard having known milk clotting activity and having the same enzyme composition of the sample.

An chymosin variant of the invention may have an altered specificity. Typically, if may have a high specific milk clotting activity (C) and a low general, i.e. non-specific, proteolytic activity (P) with regard to milk proteins. Accordingly, the C/P ratio should preferably be as high as possible, as a relatively high P-value, during the cheese manufacturing process and during maturation of the cheese will lead to the formation of low molecular peptides and free amino acids, which in turn may confer to the finished cheese an undesirable bitter taste and also result in a loss of cheese yield. As used herein, the term "C/P ratio" is defined by the methods for determining a C-value and a P-value, respectively as described in the below Examples.

The chymosin variant of the invention may have a higher C/P ratio, relative to a reference polypeptide. Such a variant may have a C/P ratio in the range of from about 1.5 to about 20, preferably a C/P ratio of at least about 3, such as at least about 5 or even at least about 10.

According to the invention, there is thus provided a variant polypeptide having chymosin activity, wherein the variant has an amino acid sequence which, when aligned with the chymosin comprising the sequence set out in SEQ ID NO: 2, comprises at least one substitution of an amino acid residue corresponding to any of amino acids 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 said positions being defined with reference to SEQ ID NO: 2 and wherein the variant has one or more altered properties as compared with a reference polypeptide having chymosin activity (such as the polypeptide of SEQ ID NO: 2).

Table 1 sets out positions that influence specific properties of the variant chymosins of the invention.

Accordingly, a variant of the invention may demonstrate decreased proteolysis in a cheese matrix or increased productivity as compared with a reference chymosin, such as the chymosin comprising the sequence set out in SEQ ID NO: 2. Such a variant may demonstrate increased specificity or reduced thermostability as compared with the chymosin comprising the sequence set out in SEQ ID NO: 2.

In particular, such a variant polypeptide of the invention may comprise an amino acid sequence which, when aligned with the sequence set out in SEQ ID NO: 2, comprises at least one substitution of an amino acid residue corresponding to any of amino acids 48, 50, 51, 61, 62, 109, 117, 126, 135, 144, 160, 161, 201, 202, 203, 221, 223, 240, 242, 244, 254, 267, 280, 292 or 295 said positions being defined with reference to SEQ ID NO: 2 and wherein the variant demonstrates increased specificity as compared with a reference polypeptide having chymosin activity.

A variant polypeptide of the invention may comprise an amino acid sequence which, when aligned with the sequence set out in SEQ ID NO: 2, comprises at least one substitution of an amino acid residue corresponding to any of amino acids 48, 50, 51, 53, 109, 126, 135, 144, 160, 201, 221, 242, 267 or 280 said positions being defined with reference to SEQ ID NO: 2 and wherein the variant demonstrates reduced temperature stability as compared with a reference polypeptide having chymosin activity.

A variant polypeptide of the invention, may demonstrate increased specific activity or an increased expression level.

Such a variant polypeptide of the invention may comprise an amino acid sequence which, when aligned with the sequence set out in SEQ ID NO: 2, comprises at least one substitution of an amino acid residue corresponding to any of amino acids 98, 109, 112, 117, 126, 135, 144, 161, 202, 203, 221, 223, 240, 244, 254, 273 or 295 said positions being defined with reference to SEQ ID NO: 2 and wherein the variant demonstrates increased specific activity as compared with a reference polypeptide having chymosin activity.

A variant polypeptide of the invention may comprise an amino acid sequence which, when aligned with the sequence set out in SEQ ID NO: 2, comprises at least one substitution of an amino acid residue corresponding to any of amino acids 50, 53, 109, 135, 144, 160, 201, 242, 267, 280 or 295 said positions being defined with reference to SEQ ID NO: 2 and wherein the variant demonstrates an increased expression level as compared with a reference polypeptide having chymosin activity.

Alternatively, a variant polypeptide of the invention may comprise an amino acid sequence which, when aligned with the sequence set out in SEQ ID NO: 2, comprises at least one substitution of an amino acid residue corresponding to any of amino acids 2, 22, 40, 76, 88, 98, 99, 112, 125, 144, 163, 187, 189, 194, 200, 223, 271, 278, 284, 289 or 294 said positions being defined with reference to SEQ ID NO: 2 and wherein the variant demonstrates decreased specificity as compared with a reference polypeptide having chymosin activity.

A variant polypeptide of the invention may comprise an amino acid sequence which, when aligned with the sequence set out in SEQ ID NO: 2, comprises at least one substitution of an amino acid residue corresponding to any of amino acids 48, 50, 53, 144, 160, 201, 242, 267 or 280 said positions being defined with reference to SEQ ID NO: 2 and wherein the variant demonstrates altered, such as increased clotting activity at pH relevant to the cheese making process, such as a low pH, as compared with a reference polypeptide having chymosin activity.

The activity of a variant may be decreased, at a pH relevant to the cheese making process, such as a low pH, as compared with a reference polypeptide having chymosin activity or at a temperature relevant to the cheese making process, such as a low temperature, as compared with a reference polypeptide having chymosin activity.

A low pH in this context may indicate a pH of less than about 6.7, for example about 6.5 or less, about 6.3 or less, such as about 6.2 or less or a lower pH.

A low temperature in this context may indicate a temperature of about 20° C. or less, for example about 15° C. or less, for example about 12° C. or less, such about 10° C. or less, such as about 6° C. or less.

A variant polypeptide of the invention may comprise an amino acid sequence which, when aligned with the sequence set out in SEQ ID NO: 2, comprises at least one substitution of an amino acid residue corresponding to any of amino acids 51, 126, 135 or 221, said positions being defined with reference to SEQ ID NO: 2 and wherein the variant demonstrates decreased proteolytic activity at low pH as compared with a reference polypeptide having chymosin activity.

A variant polypeptide of the invention may comprise an amino acid sequence which, when aligned with the sequence set out in SEQ ID NO: 2, comprises at least one substitution of an amino acid residue corresponding to any of amino acids 51, 109, 126, 135 or 221, said positions being defined with reference to SEQ ID NO: 2 and wherein the variant demonstrates decreased proteolytic activity at low temperature as compared with a reference polypeptide having chymosin activity.

A variant polypeptide of the invention may comprise an amino acid sequence which, when aligned with the sequence set out in SEQ ID NO: 2, comprises a substitution of amino acid 221, said position being defined with reference to SEQ ID NO: 2 and wherein the variant demonstrates decreased activity at low pH and/or low temperature as compared with a reference polypeptide having chymosin activity.

A preferred reference polypeptide suitable for use in the invention is the polypeptide having the sequence set out in SEQ ID NO: 2 or having at least 80% homology with SEQ ID NO: 2, for example at least 85% homology with SEQ ID NO: 2, such as a least 85% homology with SEQ ID NO: 2, such as at least 90% homology with SEQ ID NO: 2, for example at least 95%, at least 98% or at least 99% homology with SEQ ID NO: 2.

The amino acid residues in a variant chymosin of the invention that may be substituted with comparison with the sequence set out in SEQ ID NO: 2 are those which correspond to positions 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 as defined in relation to the sequence of SEQ ID NO: 2.

A variant chymosin of the invention may comprises a substitution at one or more of the said positions, for example at two, three, four, at least 5, at least 10, at least 15, at least 20, at least 25, at least 30, at least 35, at least 40, at least 45 or at least 50 or at all of the said positions.

A variant chymosin of the invention may comprise one or more substitutions as defined above. A "substitution" in this context indicates that a position in the variant which corresponds to one of the positions set out above in SEQ ID NO: 2 comprises an amino acid residue which does not appear at that position in the reference polypeptide (the reference polypeptide may be SEQ ID NO: 2).

Preferred substitutions are set out in the following Table 1 (with the positions being defined in relation to the sequence set out in SEQ ID NO: 2).

Table 1 sets out preferred substitutions, more preferred substitutions, even more preferred substitutions and most preferred substitutions. A variant of the invention may be generated using any combination of substitutions set out in Table 1 and from any of the preferred columns. In general substitutions may be selected from the most preferred substitution column.

A variant chymosin of the invention may also comprise additional modifications in comparison to the parent at positions other than those specified above, for example, one or more additional substitutions, additions or deletions. A variant of the invention may comprise a combination of different types of modification of this sort. A variant may comprise one, two, three, four, least 5, at least 10, at least 15, at least 20, at least 25, at least 30 or more such modifications (which may all be of the same type or may be different types of modification). Typically, the additional modifications may be substitutions.

TABLE 1

Preferred substitutions defined in relation to SEQ ID NO: 2

| Position | Preferred | More Preferred | Even more preferred | Most preferred | expression increased | specific activity increased | increased specificity |
|---|---|---|---|---|---|---|---|
| E2 | all AA | K Q R L V M T S A D | K Q R D | K | | | |
| L22 | all AA | I V F M | I V | I | | | |
| F40 | all AA | L I V M | L I V | L | | | |
| K48 | all AA | N T Q S I P D E R H | N T Q S | N | | | N |
| N50 | all AA | D E K R H | D E | D | D | | D |
| A51 | all AA | V T I L N S G | V T I L N G | V T I L N G | | | V T I L N G |
| K53 | all AA | Q T S A N E R H Y F G | G T S A N E | Q | Q | | |
| R61 | all AA | S Q E D K H L A G N T F | S Q E D K H | S | | | S |
| K62 | all AA | Q D E L N R H T | Q D E L | Q | | | Q |
| H76 | all AA | Q R T A H | Q R H | Q | | | |
| Y88 | all AA | L I V S A T | L I V | L | | | |
| D98 | all AA | V I S L T A G | V I S | V | | V | |
| I99 | all AA | T P V A Q S E K R D L M N | T P V A Q S | T | | | |
| E109 | all AA | Q M F L W Y N D | Q M F L W Y | Q L M | Q L | Q | Q M L |
| D112 | all AA | E N Q K R H S P T A | E N Q K R H | E N | | E | |
| A117 | all AA | S T G P V M V C L | S T G P V | S T V | | T V | S T V |
| M125 | all AA | L V F I C T | L V F I | L | | | |
| A126 | all AA | G S P T | G S P | G S | | G S | G S |
| S135 | all AA | A T G P V I E C | A T G P | T P | P | T | T P |
| N144 | all AA | D H Q K R E H A S T F G I | D H Q K E | D H Q E K | D | H K E | K E |
| N160 | all AA | D E K R H Q S G A | D E | D | D | | D |
| G161 | all AA | D E K R H Q N S A | D E | D | | D | D |
| E163 | all AA | G A D S T P Q N | G A D | G | | | |
| V187 | all AA | L M F I S T K Q N F Y A E R H | L M F I | L M | | | |
| Q189 | all AA | G E K D R A L V T S N H | G E K D R A | G E K | | | |
| T194 | all AA | S A G K R Q N | S A G | S | | | |
| I200 | all AA | V M L W Y F C | V M L W | V | | | |
| S201 | all AA | N D E K R H N A G P T | N D E | N D | D | | N D |
| G202 | all AA | D E K R H N S T P A | D E | D | | D | D |
| V203 | all AA | E D K R H Q T A N G S Y | E D | E | | E | E |
| K221 | all AA | L M V I T A S G N H Q K | L M V I T A S N H | L M V I T A S N H | | L M V I T A S N H | L M V I T A S N H |
| V223 | all AA | F I M L W Q T A S F Y | F I M W Q L | F I M W Q L | | M W Q L | F M W Q |
| Q240 | all AA | E D K R H T A S L V | E D | E | | E | E |
| Q242 | all AA | E D K R H S A T M L Y | E D | E | E | E | E |
| G244 | all AA | D E K R H A S T P | D E | D | | D | D |
| S254 | all AA | D E K R H Q N S G A P | D E | D | | D | D |

TABLE 1-continued

Preferred substitutions defined in relation to SEQ ID NO: 2

| | | | | | | | |
|---|---|---|---|---|---|---|---|
| M267 | all AA | E D K R H Q A S P G N T A | E D | E | E | | E |
| T271 | all AA | P N Q A G P | P N Q | P | | | |
| S273 | all AA | Y F T A G P Q N | Y F T | Y | | Y | |
| Q278 | all AA | K R E N D L P S T M | K R E N D | K | | | |
| Q280 | all AA | E D K R H S Y N M | E D | E | E | | E |
| T284 | all AA | S G A P M R I Y N L F V | S G A P | S | | | |
| S289 | all AA | G P A T Q E N D V | G P A T | G | | | |
| H292 | all AA | N D E K R S N A G T | N D E | D | | | D |
| Q294 | all AA | H D N P S A T | H D N | H | | | |
| K295 | all AA | L Q M E R Y F T H N | L Q M E R Y | L Q M E R Y | M R | L M E R Y | Q M E R Y |

| Position | decreased specificity | decreased temperature stability | increased clotting ability at low pH | decreased proteolytic activity at low pH | decreased proteolytic activity at low temp |
|---|---|---|---|---|---|
| E2 | K | | | | |
| L22 | I | | | | |
| F40 | L | | | | |
| K48 | | N | N | | |
| N50 | | D | D | | |
| A51 | | V T I L | | V T I | V T I L |
| K53 | | Q | Q | | |
| R61 | | | | | |
| K62 | | | | | |
| H76 | Q | | | | |
| Y88 | L | | | | |
| D98 | V | | | | |
| I99 | T | | | | |
| E109 | | Q | | | Q |
| D112 | E N | | | | |
| A117 | | | | | |
| M125 | L | | | | |
| A126 | | G | | G | G |
| S135 | | T | | T | T |
| N144 | D H Q | D | D H | | |
| N160 | | D | D | | |
| G161 | | | | | |
| E163 | G | | | | |
| V187 | L M | | | | |
| Q189 | K | | | | |
| T194 | S | | | | |
| I200 | V | | | | |

TABLE 1-continued

Preferred substitutions defined in relation to SEQ ID NO: 2

| Position | | | | | |
|---|---|---|---|---|---|
| S201 | | | D | | D |
| G202 | | | | | |
| V203 | | | | | |
| K221 | | L M V T | | M V T | M V T |
| V223 | I | | | | |
| Q240 | | | | | |
| Q242 | | E | | E | |
| G244 | | | | | |
| S254 | | | | | |
| M267 | | E | | E | |
| T271 | P | | | | |
| S273 | | | | | |
| Q278 | K | | | | |
| Q280 | | E | | E | |
| T284 | S | | | | |
| S289 | G | | | | |
| H292 | | | | | |
| Q294 | H | | | | |
| K295 | | | | | |

Table 2 sets out preferred substitutions and combinations of substitutions. That is to say, it sets out a number of preferred variants according to the invention. A variant of the invention may comprise combinations of substitutions defined in terms of the combinations of positions defined in Table 2. For example, a variant polypeptide of the invention may comprise a substitution at positions 51 and 221 (variant numbers 71 to 79) with reference to SEQ ID NO: 2. A variant of the invention may be any variant set out set out in Table 2. Table 2 is set out here and is also repeated in the Examples.

TABLE 2

Amino acid changes introduced in the protein sequence of chymosin B (SEQ ID NO: 2). Amino acids are depicted according to the single letter annotation

| Variant# | Substitutions | | | | | | |
|---|---|---|---|---|---|---|---|
| 1 | A51V | | | | | | |
| 2 | E109Q | | | | | | |
| 3 | A117S | | | | | | |
| 4 | S201N | | | | | | |
| 5 | K221L | | | | | | |
| 6 | K221M | | | | | | |
| 7 | K221V | | | | | | |
| 8 | V223F | | | | | | |
| 9 | K295Q | | | | | | |
| 10 | K48N | K53Q | R61S | K62Q | | | |
| 11 | K48N | K53Q | N144D | N160D | S201D | | |
| 12 | N50D | K53Q | N144D | N160D | S201D | Q242E | M267E | Q280E |
| 13 | L22I | | | | | | |
| 14 | F40L | | | | | | |
| 15 | H76Q | | | | | | |
| 16 | Y88L | | | | | | |
| 17 | D98V | | | | | | |
| 18 | I99T | | | | | | |
| 19 | D112N | | | | | | |
| 20 | D112E | | | | | | |
| 21 | M125L | | | | | | |

TABLE 2-continued

Amino acid changes introduced in the protein sequence of chymosin B (SEQ ID NO: 2). Amino acids are depicted according to the single letter annotation

| Variant# | Substitutions | | | | |
|---|---|---|---|---|---|
| 22 | A126G | | | | |
| 23 | S135A | | | | |
| 24 | N144D | | | | |
| 25 | N144H | | | | |
| 26 | N144Q | | | | |
| 27 | E163G | | | | |
| 28 | V187L | | | | |
| 29 | V187M | | | | |
| 30 | Q189K | | | | |
| 31 | T194S | | | | |
| 32 | I200V | | | | |
| 33 | V223I | | | | |
| 34 | T271P | | | | |
| 35 | Q278K | | | | |
| 36 | T284S | | | | |
| 37 | S289G | | | | |
| 38 | Q294H | | | | |
| 39 | E2K | | | | |
| 40 | S135T | | | | |
| 41 | Q240E | | | | |
| 42 | Y268F | | | | |
| 43 | S273Y | | | | |
| 44 | K295L | | | | |
| 45 | A51T | | | | |
| 46 | A51L | | | | |
| 47 | A51N | | | | |
| 48 | A51G | | | | |
| 49 | K221I | | | | |
| 50 | K221T | | | | |
| 51 | K221A | | | | |
| 52 | K221S | | | | |
| 53 | K221N | | | | |
| 54 | K221H | | | | |
| 55 | E109M | | | | |
| 56 | E109L | | | | |
| 57 | A117T | | | | |
| 58 | A117V | | | | |
| 59 | V223M | | | | |
| 60 | V223L | | | | |
| 61 | V223W | | | | |
| 62 | V223Q | | | | |
| 63 | K295M | | | | |
| 64 | K295E | | | | |
| 65 | K295R | | | | |
| 66 | K295Y | | | | |
| 67 | A126S | | | | |
| 68 | S135P | | | | |
| 69 | N144K | | | | |
| 70 | N144E | | | | |
| 71 | A51V | K221V | | | |
| 72 | A51V | E109Q | | | |
| 73 | A51V | A117S | | | |
| 74 | A51V | K221M | | | |
| 75 | A51V | K295Q | | | |
| 76 | K221V | E109Q | | | |
| 77 | K221V | A117S | | | |
| 78 | K221V | K295Q | | | |
| 79 | K221V | V223F | | | |
| 80 | A51V | K221V | E109Q | | |
| 81 | A51V | K221V | A117S | | |
| 82 | A51V | K221V | K295Q | | |
| 83 | A51V | K221V | V223F | | |
| 84 | A51V | K221M | K295Q | | |
| 85 | A51V | K221L | K295Q | | |
| 86 | A51V | K221M | V223F | | |
| 87 | A51V | K221L | V223F | | |
| 88 | A51V | E109Q | A117S | | |
| 89 | A51V | E109Q | K221M | | |
| 90 | K221V | E109Q | A117S | | |
| 91 | K221V | E109Q | V223F | | |
| 92 | K221V | E109Q | K295Q | | |
| 93 | K221V | A117S | V223F | | |
| 94 | K221V | A117S | K295Q | | |
| 95 | A51V | K221V | S135T | A126G | |
| 96 | A51V | K221V | S135T | A126G | S273Y |

TABLE 2-continued

Amino acid changes introduced in the protein sequence of chymosin B (SEQ ID NO: 2). Amino acids are depicted according to the single letter annotation

| Variant# | Substitutions | | | | | | | | |
|---|---|---|---|---|---|---|---|---|---|
| 97 | A51V | K221V | S135T | A126G | Q240E | | | | |
| 98 | A51V | K221V | S135T | A126G | S273Y | Q240E | | | |
| 99 | A51V | K221V | S135T | A126G | E109Q | | | | |
| 100 | A51V | K221V | S135T | A126G | K295Q | | | | |
| 101 | A51T | K221T | | | | | | | |
| 102 | A51I | K221I | | | | | | | |
| 103 | A51I | K221T | | | | | | | |
| 104 | A51T | K221T | S135T | A126G | | | | | |
| 105 | A51I | K221I | S135T | A126G | | | | | |
| 106 | A51I | K221T | S135T | A126G | | | | | |
| 107 | A51V | N50D | K53Q | N144H | N160D | S201D | Q242E | M267E | Q280E |
| 108 | K221V | N50D | K53Q | N144H | N160D | S201D | Q242E | M267E | Q280E |
| 109 | A51V | K221V | N50D | K53Q | N144H | N160D | S201D | Q242E | M267E | Q280E |
| 110 | A51V | K221V | N50D | N144H | N160D | S201D | Q242E | M267E | Q280E |
| 111 | N50D | K53Q | N160D | S201D | Q242E | M267E | Q280E | | |
| 112 | N50D | N160D | S201D | Q242E | M267E | Q280E | | | |
| 113 | H292D | G244D | S254D | G161D | G202D | Q240E | | | |
| 114 | N160D | S201D | Q242E | M267E | Q280E | H292D | G244D | S254D | G161D | V203E |
| 115 | K48N | K53Q | N144H | N160D | S201D | | | | |

A variant according to the invention (for example a variant having one or more substitution as set out in Table 1 or Table 2) may have at least about 80% homology with the reference chymosin polypeptide, such as the chymosin of SEQ ID NO: 2, for example at least about 85% homology with the parent polypeptide, such as least about 90% homology with the parent polypeptide, at least 95% homology with the parent polypeptide, at least about 98% homology with the parent polypeptide or at least about 99% homology with the parent polypeptide. Such a variant will typically have one or more substitution or sets of substitutions as set out in Table 1 or Table 2.

A variant of the invention will typically retain chymosin activity. That is to say, a variant of the invention will typically be capable of aspartic protease activity. A variant of the invention is one which is typically capable of clotting milk and which may be used in the preparation of a food product, such as a cheese.

Preferably, a variant of the invention will typically exhibit improved properties in comparison with the reference chymosin polypeptide from which it is derived. Such an improved property will typically be one which is relevant if the variant were to be used as set out below, for example in a method for preparing a cheese.

A variant which exhibits a property which is improved in relation to the reference chymosin is one which demonstrates a measurable reduction or increase in the relevant property, typically such that the variant is more suited to use as set out below, for example in a method for the production of a cheese.

The property may thus be decreased by at least 10%, at least 20%, at least 30%, at least 40% at least 50%, at least 60%, at least 70%, at least 80%, at least 90%, at least 95% or at least 99%. Alternatively, the property may be increased by at least 10%, at least 25%, at least 50%, at least 100%, at least, 200%, at least 500% or at least 1000%. The percentage decrease or increase in this context represents the percentage decrease or increase in comparison to the reference chymosin polypeptide. It is well known to the skilled person how such percentage changes may be measured—it is a comparison of the activity of the reference chymosin and the variant chymosin.

The variants described herein are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than about seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

A polypeptide of the invention may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique. A polypeptide variant according to the invention can be recovered and purified from recombinant cell cultures by methods known in the art.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptide variants according to the invention. Such fragments are considered to be encompassed within the term "a variant of the invention".

Biologically active fragments of a polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of the invention will comprise one or more of the substitutions defined herein.

The invention also features nucleic acid fragments which encode the above biologically active fragments (which biologically active fragments are themselves variants of the invention).

As set out above, the present invention provides polynucleotides encoding the variant polypeptides of the invention. The invention also relates to an isolated polynucleotide encoding at least one functional domain of a polypeptide variant of the invention. Typically, such a domain will comprise one or more of the substitutions described herein.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the parent asparaginase. Such a polypeptide will, however, typically comprise one or more of the substitutions described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well known to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent chymosin. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention.

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov/.

Another aspect of the invention pertains to vectors, preferably expression vectors, containing a nucleic acid encoding a variant chymosin polypeptide of the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. a chymosin variant of SEQ ID NO: 2, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of chymosin in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid mediated transfection or electroporation. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in E. coli with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in E. coli and other bacteria. Representative examples of appropriate host include bacterial cells, such as E. coli, Streptomyces Salmonella typhimurium and certain Bacillus species; fungal cells such as Aspergillus species, for example A. niger, A. oryzae and A. nidulans, such as yeast such as Kluyveromyces, for example K. lactis and/or Puchia, for example P. pastoris; insect cells such as Drosophila S2 and Spodoptera Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promoters suitable for use in the present invention include the promoters disclosed in WO-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

The variants of the invention, such as proteins of the present invention or functional equivalents thereof, e.g., biologically active portions and fragments thereof, can be operatively linked to a non-variant polypeptide (e.g., heterologous amino acid sequences) to form fusion proteins. A "non-variant polypeptide" in this context refers to a polypeptide having an amino acid sequence corresponding to a protein which is not substantially homologous to a variant chymosin of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the non-variant polypeptide are fused in-frame to each other. The non-variant polypeptide can be fused to the N-terminus or C-terminus of the variant polypeptide.

Expression and secretion of a variant chymosin may be enhanced by expressing the variant in the form of a fusion protein. In this context, a nucleic acid sequence may encode for a fusion protein comprising pre-prochymosin, prochymosin or chymosin. More specifically, the fusion partner may be glucoamylase or a fragment thereof. In one embodiment the pre-prochymosin, prochymosin or chymosin, or a fusion protein thereof, is secreted over the host cell membrane.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a heterologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

A fusion protein of the invention may be produced by standard recombinant DNA techniques. For example, DNA fragments coding for the different polypeptide sequences are ligated together in frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

The terms "functional equivalents" and "functional variants" are used interchangeably herein. Functional equivalents according to the invention are isolated DNA fragments that encode a polypeptide that exhibits a particular function of a variant as defined herein. Functional equivalents therefore also encompass biologically active fragments and are themselves encompassed within the term "a variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of encoded polypeptide. Accordingly, the invention provides nucleic acid molecules encoding a variant chymosin protein that contains changes in amino acid residues that are not essential for a particular biological activity. Such variant proteins differ in amino acid sequence from the parent chymosin sequence from which they are derived yet retain at least one biological activity thereof, preferably they retain at least chymosin activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the reference amino acid sequence (for example that shown in SEQ ID NO: 2).

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

The skilled person will recognise that changes can be introduced by mutation into the nucleotide sequences according to the invention thereby leading to changes in the amino acid sequence of the resulting protein without substantially altering the function of such a protein.

Accordingly, a chymosin variant of the invention is preferably a protein which comprises an amino acid sequence at least about 60%, 65%, 70%, 75%, 80%, 85%, 90%, 95%, 96%, 97%, 98%, 99% or more homologous to the reference amino acid sequence, for example that shown in SEQ ID NO: 2, and typically also retains at least one functional activity of the reference polypeptide. Variants of the invention, for example functional equivalents of a protein according to the invention, can also be identified e.g. by screening combinatorial libraries of mutants, e.g. truncation mutants, of the protein of the invention for chymosin activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having chymosin activity include, inter alia, (1) in situ hybridization (e.g. FISH) to metaphase chromosomal spreads to provide precise chromosomal location of an chymosin-encoding gene as described in Verma et al., Human Chromosomes: a Manual of Basic Techniques, Pergamon Press, New York (1988); (2) Northern blot analysis for detecting expression of chymosin mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference chymosin enzyme can be obtained by the following standard procedure:
  Mutagenesis (error-prone, doped oligo, spiked oligo) or synthesis of variants
  Transformation in, for example *K. lactis*
  Cultivation of transformants, selection of transformants
  Expression
  Optional purification and concentration
  Primary Screening
  Identification of an improved variant (for example in relation to specific activity)

In one embodiment the invention relates to a method of producing a chymosin polypeptide variant according to the invention, which method comprises:
  a) selecting a reference chymosin polypeptide;
  b) substituting at least one amino acid residue corresponding to any of
  2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295
  said positions being defined with reference to SEQ ID NO: 2;
  c) optionally substituting one or more further amino acids as defined in b);
  d) preparing the variant resulting from steps a)-c);
  e) determining a property of the variant, for example as set out in the Examples; and
  f) selecting a variant an altered property in comparison to the reference chymosin polypeptide.

In a preferred embodiment in the method of producing a chymosin polypeptide variant according to the invention, the reference chymosin polypeptide has the sequence set out in SEQ ID NO: 2.

More preferably in step b) of the method according to the invention at least one amino acid residue corresponding to any of 2, 22, 40, 48, 50, 51, 53, 61, 62, 76, 88, 98, 99, 109, 112, 117, 125, 126, 135, 144, 160, 161, 163, 187, 189, 194, 200, 201, 202, 203, 221, 223, 240, 242, 244, 254, 267, 271, 273, 278, 280, 284, 289, 292, 294 or 295 is substituted, said positions being defined with reference to SEQ ID NO: 2. The reference polypeptide may have at least about 80% homology with SEQ ID NO: 2.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from yeasts, for example, *K. lactis*. Host cells also include, but are not limited to, mammalian cell lines such as CHO, VERO, BHK, HeLa, COS, MDCK, 293, 3T3, WI38, and choroid plexus cell lines.

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* and *Bacillus thu-ringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Klyuveromyces* spp. including *Klyuveromyces lactis*.

Suitable host organisms among filamentous fungi include species of *Acremonium, Aspergillus, Fusarium, Humicola, Mucor, Myceliophtora, Neurospora, Penicillium, Thielavia, Tolypocladium* or *Trichoderma*, such as e.g. *Aspergillus aculeatus, Aspergillus awamori, Aspergillus foetidus, Aspergillus japonicus, Aspergillus oryzae, Aspergillus nidulans* or *Aspergillus niger*, including *Aspergillus nigervar. awamori, Fusarium bactridioides, Fusa-rium cereals, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichiodes, Fusarium sulphureum, Fusarium torulosum, Fusarium trichothecioides, Fusarium venenatum, Humicola insolens, Humicola langinosa, Mucor miehei, Myceliophtora thermophila, Neurospora crassa, Penicillium chrysogenum, Penicillium camenbertii, Penicillium purpurogenum, Rhizomucor miehei, Thielavia terrestris, Trichoderma harzianum, Trichoderma koningii, Trichoderma longibrachiatum, Trichoderma reesii* or *Trochoderma viride*.

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

The present invention further discloses a composition comprising the chymosin variants according to the invention. The composition may optionally comprise other ingredients such as e.g. other enzymes such as a pepsin. Such a composition may comprises the variant polypeptide of the invention or one obtainable by a method of the invention for identifying a variant chymosin.

In addition to the variant chymosin, and one or more additional enzymes, if present, a composition according to the invention may comprise additives that are conventionally used in rennets of animal origin such as e.g. NaCl.

The invention further relates to use of a variant polypeptide of the invention or a composition of the invention in the preparation of a cheese. Accordingly, the invention concerns a process for the production of a cheese, which method comprises comprising adding a milk clotting effective amount of a variant polypeptide or a composition of the invention to milk and carrying out appropriate further cheese manufacturing steps.

That is to say, the invention provides a process for preparing cheese, comprising, (i) supplementing milk with a chymosin variant or composition according to the invention, to effect coagulation of the milk, wherein a curd is obtained; and (ii) processing the curd into cheese.

In such a method of manufacturing cheese from milk, the milk may be cow's milk, camel's milk, buffalo milk, goat's milk, sheep's milk and a mixture of any such milk types.

The invention relates to a cheese obtainable by such a process.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Materials & Methods
Medium Composition

YEP2D medium: 10 g/l yeast extract, 20 g/l bacto-peptone, 40 g/l glucose. pH was set to pH 6.7 with 4N NaOH. Medium was autoclaved for 30 minutes at 110° C.

YEP2D/MES medium: 10 g/l yeast extract, 20 g/l bacto-peptone, 40 g/l glucose, 20 g/l MES. pH was set to pH 6.7 with 4N NaOH. Medium was autoclaved for 30 minutes at 110° C.

YEP2D plates contain YEP2D medium with 1.8-2% agar. Medium was autoclaved for 30 minutes at 110° C. and poured in petridishes.

Buffer Composition

NaOH-MES buffer: prepare MES-buffer at pH 6.05 containing 50 g/kg MES and dilute 1 volume of 4 N NaOH with 7 volumes of the MES buffer.

Strains

GG799: This *Kluyveromyces lactis* strain is used as a wild-type strain. This strain is obtained from New England Biolabs, Ipswich, Mass., USA Molecular Biology Techniques Molecular biology techniques known to the skilled person were used (see: Sambrook & Russell, *Molecular Cloning: A Laboratory Manual*, 3rd Ed., CSHL Press, Cold Spring Harbor, N.Y., 2001). Examples of the general design of expression vectors for gene over expression, transformation, use of markers and selective media can be found in WO2007060247, WO2010102982 and U.S. Pat. No. 4,943,529 and references herein.

Chymosin Quantification

The internal standard (ISTD) WIL*GDVFIREYYSV*FDR was ordered from CPC Scientific (Sunnyvale, Calif., USA) and contained L*6×$^{13}$C 1×$^{15}$N and V*5×$^{13}$C 1×$^{15}$N. The ISTD contained an internal trypsin cleavage site in order to monitor the digestion with trypsin to completion.

Proteins were precipitated from the samples (100 µl) by 1:1 dilution in 20% TCA in aceton −20° C. and incubation for 60 minutes at −20° C. Proteins were pelleted by centrifugation for 20 minutes at 5251×g, 4° C. The supernatant was carefully discarded and the pellet was washed with 300 µl aceton −20° C. Proteins were pelleted by centrifugation for 10 minutes at 5251×g, 4° C. The supernatant was carefully discarded and the pellets were dissolved in 50 µl 50 mM NaOH. ISTD (10 µl, 7.96 pMol) in 100 mM NH$_4$HCO$_3$ and 100 mM NH$_4$HCO$_3$ (390 µl) were added to the samples. 500 mM DTT (5 µl) in 100 mM NH$_4$HCO$_3$ was added and samples were incubated for 30 minutes at 25° C. 550 mM IAA (10 µl) in 100 mM NH$_4$HCO$_3$ was added and samples were incubated for 30 minutes at 21° C. in the dark. 15 µl 1 mg/ml Trypsin (Worthington) in 0.01 N HCl pH3 was added and samples were digested by incubation at 37° C. overnight. Another 3 µl 1 mg/ml Trypsin in 0.01 N HCl pH3 was added to complete the digestion by incubation at 37° C. for three more hours. The digests were acidified with formic acid (FA, 5 µl). Samples were full loop injected (5 µl) on an Accela-LTQ-Velos (Thermo Fisher Scientific, Waltham Mass., USA).

LC-MS/MS was performed with the following parameters:

Buffer A: 0.1% FA, Buffer B: 0.1% FA in AcN (both U-HPLC grade, Biosolve, Valkenswaard, The Netherlands)

Column: Zorbax XDB-C18 1.8 µm 2.1×50 mm with guard column (Agilent, Santa Clara, Calif., USA)

Column temperature 50° C.

Gradient: 0-5 minutes 10%-50% B, 5-6.5 minutes 80% B, 6.5-8 minutes 10% B. Flow rate: 0-5 minutes 400 µl/min, 5-7.5 minutes 600 µl/min, 7.5-8 minutes 400 µl/min MS method consisted of 3 scan segments:

Scan segment 1: 0-2.8 min. ITMS+c norm (539.84)→(145.0-2000.0), ITMS+c norm (542.95)→(145.0-2000.0), MS/MS: AT CID CE 35.0%, Q 0.250, Time 10.000, IsoW 2.0, CV=0.0V.

Scan segment 2: 2.8-4.1 min. ITMS+c norm (559.90)→(150.0-2000.0), ITMS+c norm (563.52)→(155.0-2000.0), MS/MS: AT CID CE 35.0%, Q 0.250, Time 10.000, IsoW 2.0, CV=0.0V.

Scan segment 3: 4.1-8 min. ITMS+c norm (727.04)→(200.0-2000.0), ITMS+c norm (731.37)→(200.0-2000.0), MS/MS: AT CID CE 35.0%, Q 0.250, Time 10.000, IsoW 2.0, CV=0.0V.

Quantification was performed by determining the ratio of the LC-MS/MS area of the native chymosin peptide and the LC-MS/MS area of the cleaved ISTD (EYYSV*FDR). Peak area determination was performed using QuanBrowser (Thermo Fisher Scientific, Waltham Mass., USA).

Clotting Activity (C)

A milk solution was prepared by adding 11 gram of Nilac milk powder (NIZO Food Science, Ede, the Netherlands) to 100 ml 4.5 mM CaCl2 (resulting pH 6.6). The solution was stirred for 30 minutes and kept in the dark for another 30 minutes. The milk is then ready and was used within half an hour. Subsequently, 5 ml milk solution was added to a test tube and pre-incubated for 5 minutes in a water bath of 32° C. The reaction was started by adding 100 µl enzyme to the milk solution. The milk clotting was followed visually in time. The moment coagulation starts is the point of clotting time. Different amounts of a diluted and purified Maxiren 1800 preparation (DSM Food-Specialties, Delft, the Netherlands) was used to obtain the reference curve for activity determination. 100 mg Maxiren 1800 was dissolved in 15 ml H2O, concentrated and washed out with H2O and 40 mM MES-NaOH, pH 5.7 using an Amicon Ultra centrifugal filter, 10 kDa. The final volume was adjusted to 5 ml. A series of clotting measurements at different concentrations was performed (set at 2, 4, 6, 8, 10, 12, 15 and 20 IMCU/ml in the Maxiren stock solution) and clotting time for each dilution was determined and the relation between the clotting time and the amount of units in the assay was determined. The clotting time found in the tested samples was calculated back to the IMCU activity of the original Maxiren stock solution, determined with this assay, and expressed in U/ml. This milk-clotting activity of the tested samples was used in the calculation of the C/P (see Example 3).

General Proteolytic Activity (P)

Proteolytic activity was estimated using casein sodium salt from bovine milk (Sigma, C8654) as substrate. The reaction mix (750 µl) contained: 730 µl substrate (0.5% casein sodium salt in 33 mM MES, pH 5.8) and 20 µl sample to be tested. The reaction mix was incubated for 120 min at 32° C. and the reaction was terminated by addition of 250 µl 12% (w/w) TCA with vigorous stirring on a vortex mixer. To determine OD280 (t=0 min) the reaction was stopped immediately after start. The OD280 of the supernatants was measured after centrifugation at 12,000 rpm for 10 min. The difference (deltaOD) between OD280 (t=120 min) and OD280 (t=0 min) was calculated and is a measurement of the proteolytic activity at pH5.8 in the tested samples. The proteolytic activity (P) was calculated back to the original sample concentration by multiplying with a factor 50 and used for the calculation of the C/P (see Example 3).

For examples 8 and 9 a different method to detect the proteolytic activity was used. Proteolytic activity was estimated using QuantiCleave Protease assay kit (Thermo Scientific—Pierce) according to manufacturers' instructions with some small changes. The chymosin samples to be tested were diluted in 40 mM MES, pH 5.7 up to 20 IMCU/ml. The reaction mix contained: 125 µl succinylated casein solution (0.2% (w/v)) in 40 mM MES buffer at the preferred pH and 25 µl of the diluted chymosin sample. The reaction mix was incubated for 60 min at the preferred temperature and 50 µl TNBSA working solution in 0.5 M borate buffer pH 8.5 were added to react with exposed primary amines. After 120 min incubation at room temperature the intensity of the orange-yellow product was measured at 405 nm. Blanks contained the same components as reaction but without substrate and were treated the same way. Final results were corrected for the value measured in the blanks.

Example 1: DNA Constructs and Transformation

Synthetic DNA constructs were designed to start with a XhoI restriction site, encoding amino acids L and E, followed in frame with DNA encoding a kex-protease cleavage site with amino acids K and R, followed by in frame genes encoding variants of bovine pro-chymosin B starting with amino acids A, E, I and T, ending with a PacI restriction site just after the stop codon. As an example, a DNA fragment encoding the wild type pro-chymosin B sequence is listed as SEQ ID NO: 1. Codon usage was adapted according to the method described in patent application US090286280. All variants were designed in a similar fashion and cloned as XhoI PacI fragments in vector pKLAC1 (New England Biolabs, Ipswich, Mass., USA).

The resulting open reading frames start with the leader sequence of the *K. lactis* Mating Factor alpha and progresses over the kex processing site to the bovine pro-chymosin B variants. Amino acid changes that were introduced in the 135 variants are depicted in Table 2. Position of the change is indicated in comparison with the mature chymosin B sequence (SEQ ID NO: 2). Some amino acid positions are changed into various different amino acids, like position 221 (variant #5, 6 and 7) and position 295 (variant #9 and 44), to test if different changes at these positions have a similar or different effect. Some other variants have multiple changes introduced into the amino acid sequence of the chymosin protein, like variant #10, 11 and 12. A wild-type gene encoding the unchanged pro-chymosin protein was also used in gene cloning and transformation and was later used to compare with enzymes made with the variant genes.

TABLE 2

Amino acid changes introduced in the protein sequence of chymosin B.
Aminoacids are depicted according to the single letter annotation

| Variant# | Mutations | | | | | | | |
|---|---|---|---|---|---|---|---|---|
| 1 | A51V | | | | | | | |
| 2 | E109Q | | | | | | | |
| 3 | A117S | | | | | | | |
| 4 | S201N | | | | | | | |
| 5 | K221L | | | | | | | |
| 6 | K221M | | | | | | | |
| 7 | K221V | | | | | | | |
| 8 | V223F | | | | | | | |
| 9 | K295Q | | | | | | | |
| 10 | K48N | K53Q | R61S | K62Q | | | | |
| 11 | K48N | K53Q | N144D | N160D | S201D | | | |
| 12 | N50D | K53Q | N144D | N160D | S201D | Q242E | M267E | Q280E |
| 13 | L22I | | | | | | | |
| 14 | F40L | | | | | | | |
| 15 | H76Q | | | | | | | |
| 16 | Y88L | | | | | | | |
| 17 | D98V | | | | | | | |
| 18 | I99T | | | | | | | |
| 19 | D112N | | | | | | | |
| 20 | D112E | | | | | | | |
| 21 | M125L | | | | | | | |
| 22 | A126G | | | | | | | |
| 23 | S135A | | | | | | | |
| 24 | N144D | | | | | | | |
| 25 | N144H | | | | | | | |
| 26 | N144Q | | | | | | | |
| 27 | E163G | | | | | | | |
| 28 | V187L | | | | | | | |
| 29 | V187M | | | | | | | |
| 30 | Q189K | | | | | | | |
| 31 | T194S | | | | | | | |
| 32 | I200V | | | | | | | |
| 33 | V223I | | | | | | | |
| 34 | T271P | | | | | | | |
| 35 | Q278K | | | | | | | |
| 36 | T284S | | | | | | | |
| 37 | S289G | | | | | | | |
| 38 | Q294H | | | | | | | |
| 39 | E2K | | | | | | | |
| 40 | S135T | | | | | | | |
| 41 | Q240E | | | | | | | |
| 42 | Y268F | | | | | | | |

TABLE 2-continued

Amino acid changes introduced in the protein sequence of chymosin B.
Aminoacids are depicted according to the single letter annotation

| Variant# | Mutations | | | | | | | | | |
|---|---|---|---|---|---|---|---|---|---|---|
| 43 | S273Y | | | | | | | | | |
| 44 | K295L | | | | | | | | | |
| 45 | A51T | | | | | | | | | |
| 46 | A51L | | | | | | | | | |
| 47 | A51N | | | | | | | | | |
| 48 | A51G | | | | | | | | | |
| 49 | K221I | | | | | | | | | |
| 50 | K221T | | | | | | | | | |
| 51 | K221A | | | | | | | | | |
| 52 | K221S | | | | | | | | | |
| 53 | K221N | | | | | | | | | |
| 54 | K221H | | | | | | | | | |
| 55 | E109M | | | | | | | | | |
| 56 | E109L | | | | | | | | | |
| 57 | A117T | | | | | | | | | |
| 58 | A117V | | | | | | | | | |
| 59 | V223M | | | | | | | | | |
| 60 | V223L | | | | | | | | | |
| 61 | V223W | | | | | | | | | |
| 62 | V223Q | | | | | | | | | |
| 63 | K295M | | | | | | | | | |
| 64 | K295E | | | | | | | | | |
| 65 | K295R | | | | | | | | | |
| 66 | K295Y | | | | | | | | | |
| 67 | A126S | | | | | | | | | |
| 68 | S135P | | | | | | | | | |
| 69 | N144K | | | | | | | | | |
| 70 | N144E | | | | | | | | | |
| 71 | A51V | K221V | | | | | | | | |
| 72 | A51V | E109Q | | | | | | | | |
| 73 | A51V | A117S | | | | | | | | |
| 74 | A51V | K221M | | | | | | | | |
| 75 | A51V | K295Q | | | | | | | | |
| 76 | K221V | E109Q | | | | | | | | |
| 77 | K221V | A117S | | | | | | | | |
| 78 | K221V | K295Q | | | | | | | | |
| 79 | K221V | V223F | | | | | | | | |
| 80 | A51V | K221V | E109Q | | | | | | | |
| 81 | A51V | K221V | A117S | | | | | | | |
| 82 | A51V | K221V | K295Q | | | | | | | |
| 83 | A51V | K221V | V223F | | | | | | | |
| 84 | A51V | K221M | K295Q | | | | | | | |
| 85 | A51V | K221L | K295Q | | | | | | | |
| 86 | A51V | K221M | V223F | | | | | | | |
| 87 | A51V | K221L | V223F | | | | | | | |
| 88 | A51V | E109Q | A117S | | | | | | | |
| 89 | A51V | E109Q | K221M | | | | | | | |
| 90 | K221V | E109Q | A117S | | | | | | | |
| 91 | K221V | E109Q | V223F | | | | | | | |
| 92 | K221V | E109Q | K295Q | | | | | | | |
| 93 | K221V | A117S | V223F | | | | | | | |
| 94 | K221V | A117S | K295Q | | | | | | | |
| 95 | A51V | K221V | S135T | A126G | | | | | | |
| 96 | A51V | K221V | S135T | A126G | S273Y | | | | | |
| 97 | A51V | K221V | S135T | A126G | Q240E | | | | | |
| 98 | A51V | K221V | S135T | A126G | S273Y | Q240E | | | | |
| 99 | A51V | K221V | S135T | A126G | E109Q | | | | | |
| 100 | A51V | K221V | S135T | A126G | K295Q | | | | | |
| 101 | A51T | K221T | | | | | | | | |
| 102 | A51I | K221I | | | | | | | | |
| 103 | A51I | K221T | | | | | | | | |
| 104 | A51T | K221T | S135T | A126G | | | | | | |
| 105 | A51I | K221I | S135T | A126G | | | | | | |
| 106 | A51I | K221T | S135T | A126G | | | | | | |
| 107 | A51V | N50D | K53Q | N144H | N160D | S201D | Q242E | M267E | Q280E | |
| 108 | K221V | N50D | K53Q | N144H | N160D | S201D | Q242E | M267E | Q280E | |
| 109 | A51V | K221V | N50D | K53Q | N144H | N160D | S201D | Q242E | M267E | Q280E |
| 110 | A51V | K221V | N50D | N144H | N160D | S201D | Q242E | M267E | Q280E | |
| 111 | N50D | K53Q | N160D | S201D | Q242E | M267E | Q280E | | | |
| 112 | N50D | N160D | S201D | Q242E | M267E | Q280E | | | | |
| 113 | H292D | G244D | S254D | G161D | G202D | Q240E | | | | |
| 114 | N160D | S201D | Q242E | M267E | Q280E | H292D | G244D | S254D | G161D | V203E |
| 115 | K48N | K53Q | N144H | N160D | S201D | | | | | |

Transformation and strain selection were performed by electroporation and selection on acetamide containing plates essentially as described in WO2007060247. The plasmids were linearized by digestion with SacII and transformed to *Kluyveromyces lactis* strain GG799 by electroporation. Of each construct six transformants were tested for chymosin production using shake flask fermentations, and the best producing transformant was selected for further analysis Example 2: Cultivation, Activation and Concentration The *Kluyveromyces lactis* strains harbouring a mutant bovine pro-chymosin gene were placed on YEP2D agar plate and grown for 48 hours at 30° C. A pre-culture in 20 ml of YEP2D medium in 100 ml Erlenmeyer flasks was inoculated with the yeast cells taken from the plates. The cultures were grown for 24 hours in an incubator shaker at 30° C. and 250 rpm. The amount of pre-culture for inoculation of new 500 ml Erlenmeyer flasks with 100 ml YEP2D/MES medium was calculated to give a final OD600=0.01. These main cultures were grown for 65 hours in an incubator shaker at 30° C. and 250 rpm. For strain conservation 2 ml of pre-culture were centrifuged (4000 rpm and 10 min), cell pellet was suspended in 0.7 ml 70% glycerol and stored at −60° C.

Pro-chymosin was converted (activated) into mature chymosin by a pH step as described below. 35 g of the broth of the main culture after 65 hours cultivation was centrifuged at 8000 rpm for 15 minutes (10° C.) and 17 ml of the supernatant was used for activation of pro-chymosin. Activation was done by adding diluted hydrochloric acid (1 N) in small aliquots (typically by adding the 1N HCl in 50-200 µl volume) to the sample ensuring good mixing to avoid local pH effects. The pH of the sample was adjusted to 2.35-2.40. After 30-90 minutes incubation at 30° C. the pH was adjusted to 6.05±0.05 with MES-NaOH buffer.

Activated chymosin samples were 20 times concentrated and the medium components were washed out with 40 mM MES-NaOH, pH 5.7 using diafiltration. For this an Amicon Ultra centrifugal filter, 10 kDa was used. The starting volume of the activated sample was 20 ml and the volume of the final concentrated sample was 1 ml. The samples were formulated by addition of 1 ml glycerol. The extent of the final concentration was therefore 10-fold compared to the initial chymosin concentration. These samples were used for measuring the activity and chymosin protein concentration (Examples 3 and 4). To analyze the chymosin expression level and to check the extend of the activation the samples were loaded on a 4-12% gradient SDS-PAGE (NuPAGE 4-12% Bis-Tris Gel, Invitrogen). The following molecular weight marker was used: SeeBlue Plus2 Pre-Stained Standard, Invitrogen (188, 98, 62, 49, 38, 28, 17, 14, 7, 3 kDa). Activation of pro-chymosin seemed to be complete in all variant chymosins.

Example 3: Activity Determination

The specificity of chymosin (C/P) is an important parameter for the functional properties of the enzyme in the cheese making process. The specificity of an individual chymosin sample can be calculated by dividing the milk clotting activity (C) by the general proteolytic activity (P). This value is than divided by the C/P that is measured for the control sample Maxiren, to obtain the relative C/P. The method to measure the C and P activity is described in Materials and Methods section. As can be seen in Table 3, various variants have a relative C/P ratio higher than 1.0, indicating they have a higher C/P compared to the control chymosin Maxiren. Also a number of mutants have a lower relative C/P ratio than Maxiren (Table 4).

TABLE 3

Higher relative C/P calculated for different chymosin variants

| Variant # | Rel. C/P |
|---|---|
| 1 | 5.3 |
| 2 | 1.2 |
| 3 | 1.2 |
| 4 | 1.2 |
| 5 | 1.2 |
| 6 | 1.4 |
| 7 | 4.1 |
| 8 | 1.0 |
| 9 | 1.1 |
| 10 | 1.2 |
| 11 | 1.2 |
| 12 | 2.0 |
| 45 | 2.0 |
| 46 | 18.3 |
| 47 | 2.7 |
| 48 | 1.2 |
| 49 | 3.8 |
| 50 | 3.0 |
| 51 | 1.8 |
| 52 | 2.8 |
| 53 | 1.8 |
| 54 | 1.9 |
| 55 | 5.6 |
| 56 | 2.2 |
| 57 | 2.1 |
| 58 | 3.2 |
| 59 | 1.1 |
| 61 | 2.8 |
| 62 | 1.6 |
| 63 | 1.2 |
| 64 | 1.9 |
| 65 | 1.1 |
| 66 | 1.4 |
| 67 | 1.2 |
| 68 | 1.6 |
| 69 | 1.1 |
| 70 | 1.5 |
| 71 | 16.8 |
| 72 | 7.1 |
| 73 | 4.9 |
| 74 | 12.2 |
| 75 | 5.3 |
| 76 | 5.1 |
| 77 | 3.7 |
| 78 | 3.8 |
| 79 | 3.1 |
| 80 | 19.9 |
| 81 | 43.8 |
| 82 | 10.4 |
| 83 | 6.6 |
| 84 | 8.3 |
| 85 | 9.1 |
| 86 | 6.6 |
| 87 | 7.7 |
| 88 | 4.3 |
| 89 | 23.1 |
| 90 | 9.1 |
| 91 | 8.1 |
| 92 | 5.9 |
| 93 | 5.5 |
| 94 | 6.2 |
| 95 | 25.8 |
| 96 | 16.8 |
| 97 | 7.2 |
| 98 | 15.1 |
| 99 | 43.8 |
| 100 | 9.5 |
| 101 | 8.8 |
| 103 | 23.1 |
| 104 | 27.4 |

TABLE 3-continued

Higher relative C/P calculated for different chymosin variants

| Variant # | Rel. C/P |
|---|---|
| 105 | 31.3 |
| 106 | 43.8 |
| 107 | 13.7 |
| 108 | 5.8 |
| 109 | 10.4 |
| 110 | 23.1 |
| 111 | 2.4 |
| 112 | 1.6 |
| 113 | 2.9 |
| 114 | 2.5 |
| 115 | 1.5 |

TABLE 4

Lower relative C/P calculated for different chymosin variants

| Variant # | Rel. C/P |
|---|---|
| 13 | 0.6 |
| 14 | 0.7 |
| 15 | 0.8 |
| 16 | 0.6 |
| 17 | 0.5 |
| 18 | 0.6 |
| 19 | 0.5 |
| 20 | 0.8 |
| 21 | 0.7 |
| 22 | 0.6 |
| 23 | 0.6 |
| 24 | 0.6 |
| 25 | 0.7 |
| 26 | 0.6 |
| 27 | 0.6 |
| 28 | 0.6 |
| 29 | 0.6 |
| 30 | 0.4 |
| 31 | 0.6 |
| 32 | 0.6 |
| 33 | 0.6 |
| 34 | 0.7 |
| 35 | 0.7 |
| 36 | 0.6 |
| 37 | 0.7 |
| 38 | 0.5 |
| 39 | 0.7 |

Example 4: Specific Activity

Chymosin was quantified with LC-MS, using an experimental procedure adapted from the Absolute Quantification (AQUA) method (Gerber et al 2003).

The synthetic internal standard containing stable heavy isotopes was used for quantification and method development. Quantification of chymosin was based on peptide EYYSVFDR (isotope labelled internal standard; ISTD). The standard was scaled by NMR quantification prior to the experiments to ensure that the correct absolute amount internal standard was added.

Samples as described in Example 2 were processed by TCA precipitation as described in the Materials and Methods section. The protein pellets were solubilized in 8M urea containing the internal standard. Samples were diluted to <2M urea with $NH_4HCO_3$ and trypsin was added for proteolytic digestion. Samples were analyzes using an Accela-LTQ-Orbitrap. Quantification was performed by calculation of the areas of the signals from the ISTD and chymosin peptides based on unique fragment ions of each peptide. The ratio of these areas provided the chymosin concentration, since the internal standard was spiked in a known amount and the chymosin peptide was equimolar to the intact chymosin due to complete digestion with trypsin.

The specific activity of the different chymosin variants was estimated by measuring the milk clotting activity and dividing this by the chymosin protein content of the preparation. The milk clotting activity of the individual samples was determined as described in the Materials and Methods section. The relative specific activity of the variants was calculated by dividing the specific activity of the chymosin variants by the specific activity that was measured for the control chymosin Maxiren. As can be seen in Table 5, a number of chymosin variants show a clear increase in the relative specific activity of the enzyme.

TABLE 5

Determination of the relative specific activity of chymosin variants

| Variant # | Rel. Spec. Act. |
|---|---|
| 2 | 1.2 |
| 5 | 1.8 |
| 6 | 2.0 |
| 7 | 1.5 |
| 17 | 1.1 |
| 20 | 1.1 |
| 22 | 1.6 |
| 25 | 1.4 |
| 40 | 2.0 |
| 41 | 1.2 |
| 43 | 1.5 |
| 44 | 1.1 |
| 49 | 1.6 |
| 50 | 1.7 |
| 51 | 1.6 |
| 52 | 2.0 |
| 53 | 2.5 |
| 54 | 2.1 |
| 57 | 2.8 |
| 58 | 1.9 |
| 59 | 4.2 |
| 60 | 1.8 |
| 61 | 1.2 |
| 62 | 1.1 |
| 63 | 1.7 |
| 64 | 1.7 |
| 65 | 1.2 |
| 66 | 1.2 |
| 67 | 1.1 |
| 69 | 1.4 |
| 70 | 1.4 |
| 71 | 3.5 |
| 74 | 2.3 |
| 75 | 1.5 |
| 76 | 2.9 |
| 77 | 1.8 |
| 78 | 2.5 |
| 79 | 2.6 |
| 80 | 1.9 |
| 81 | 1.9 |
| 82 | 1.3 |
| 83 | 1.5 |
| 84 | 2.0 |
| 85 | 2.1 |
| 86 | 1.9 |
| 87 | 1.4 |
| 90 | 2.7 |
| 91 | 2.4 |
| 92 | 6.9 |
| 93 | 2.3 |
| 94 | 1.4 |
| 98 | 3.5 |
| 101 | 2.3 |
| 102 | 1.5 |
| 103 | 1.8 |
| 104 | 1.9 |

TABLE 5-continued

Determination of the relative specific activity of chymosin variants

| Variant # | Rel. Spec. Act. |
|---|---|
| 105 | 1.5 |
| 106 | 1.1 |
| 107 | 1.3 |
| 108 | 1.5 |
| 109 | 2.7 |
| 110 | 3.4 |
| 111 | 1.3 |
| 112 | 1.5 |
| 113 | 1.4 |
| 114 | 2.3 |

Example 5: Productivity

The measured protein content in all samples, as determined as described in Example 4 was compared to the protein content in a sample produced with the wild-type chymosin gene. The protein content in these samples can be used as an indication of the productivity of the different variant in shake flask since each sample was treated similarly. The relative productivity compared to wild type chymosin was calculated by dividing the two numbers. From this it became clear that variants that contained additional negative surface-charge, like variant #12, and #107, #111 and #112 had a clearly higher productivity than wild-type chymosin (Table 6). These variants have multiple changes in the amino acid sequence of chymosin which has led to the introduction of extra negative charges (aspartate and glutamate) in the amino acid sequence of calf chymosin (Table 2).

TABLE 6

Determination of the relative productivity of chymosin variants

| Variant # | Rel. productivity |
|---|---|
| 12 | 3.5 |
| 56 | 1.1 |
| 63 | 1.3 |
| 65 | 1.1 |
| 68 | 1.1 |
| 72 | 2.3 |
| 89 | 2.3 |
| 107 | 2.9 |
| 111 | 2.4 |
| 112 | 2.1 |

Example 6: Temperature Stability

For measuring the thermostability of the different chymosin variants, samples as produced in example 2 were diluted to a clotting activity of 10 U/ml in 40 mM MES pH 5.7. The diluted samples were than incubated at 45, 50, 55, 60, 65 and 70 degrees C. for 10 minutes. After this incubation the samples were cooled and the residual activity was measured using the milk clotting assay described in Materials and Methods. The milk clotting activity was compared to a sample of Maxiren that was treated similarly. Additionally, a sample of Chymax M (Chr. Hansen) was used in these experiments. Table 7 shows the residual milk clotting activity of a number of chymosin variants after the incubation. All of the most thermolabile variants (95, 98 and 104) contain the mutations S135T and A126G. These mutations may therefore be involved in thermolability. Chymax M was found to be much more thermostabile than Maxiren and the variants derived from calf chymosin B. A low thermostability is preferable to completely inactivate the enzyme during pasteurization and/or in the cooking or stretching/molding step in the production of specific cheeses.

TABLE 7

Temperature stability of chymosin variants

| Temperature | 45 | 50 | 55 | 60 | 65 | 70 |
|---|---|---|---|---|---|---|
| Maxiren | 100 | 103 | 91 | 81 | 15 | 0 |
| Chymax M | 100 | 94 | 97 | 94 | 85 | 0 |
| 5 | 100 | 97 | 97 | 46 | 0 | 0 |
| 6 | 100 | 97 | 97 | 50 | 3 | 0 |
| 7 | 100 | 100 | 91 | 43 | 0 | 0 |
| 11 | 100 | 102 | 103 | 50 | 0 | 0 |
| 12 | 100 | 97 | 95 | 41 | 0 | 0 |
| 46 | 100 | 100 | 95 | 44 | 0 | 0 |
| 71 | 100 | 100 | 87 | 42 | 0 | 0 |
| 74 | 100 | 100 | 97 | 56 | 3 | 0 |
| 80 | 100 | 98 | 85 | 35 | 0 | 0 |
| 89 | 100 | 100 | 92 | 41 | 0 | 0 |
| 95 | 100 | 97 | 77 | 11 | 0 | 0 |
| 98 | 100 | 100 | 81 | 12 | 0 | 0 |
| 103 | 100 | 97 | 95 | 44 | 0 | 0 |
| 104 | 100 | 100 | 88 | 23 | 0 | 0 |
| 106 | 100 | 100 | 90 | 37 | 0 | 0 |

Example 7: Milk Clotting Activity at Lower pH

The activity of the different chymosin variants was determined using an adaptation of the milk clotting method as described in Material and Methods, by adjusting the pH of the milk solution to different pH's by addition of lactic acid or NaOH respectively. All chymosin samples that were tested were diluted to 10 U/ml in 40 mM MES pH 5.7, before testing the clotting activity in the various pH adjusted milk solutions. Results were compared with the Maxiren milk clotting activity and are depicted in Table 8. Milk clotting activity at pH6.6 was set at 1.0 and all other results were related to this number. Variant #11, 12 and 107, all with increased negative surface charge, show increased clotting activity at lower pH, compared to the milk clotting activity of the control commercial chymosins Maxiren and Chymax M. Besides this, several variants show decreased clotting activity compared to Maxiren at lower pH. All of these variants have a change at amino acid position 221 of the mature chymosin sequence.

TABLE 8 pH dependence of milk clotting activity

| pH | 5.8 | 6 | 6.2 | 6.4 | 6.6 | 6.8 |
|---|---|---|---|---|---|---|
| Maxiren | 3.7 | 3.1 | 2.5 | 1.7 | 1.0 | 0.5 |
| Chymax M | 3.5 | 2.8 | 2.1 | 1.5 | 1.0 | 0.5 |
| 11 | 5.8 | 4.2 | 2.6 | 1.8 | 1.0 | 0.6 |
| 12 | 6.6 | 5.0 | 3.5 | 2.1 | 1.0 | 0.6 |
| 107 | 5.3 | 4.2 | 3.2 | 2.0 | 1.0 | 0.5 |

Example 8: Proteolytic Activity at Reduced Temperature

Cheese ripening often occurs at reduced temperatures, and it is therefore relevant to estimate the proteolytic activity of the different chymosin variants at reduced temperatures. Since many of the variants show very low proteolytic activity, we decided to use a different, more sensitive, method for measurement of the proteolysis of casein. This method was performed at pH5.0, more similar to the pH that is relevant for cheese ripening. Proteolytic activity at different temperatures was estimated using QuantiCleave Protease assay kit as described in Materials & Methods section with incubation for 60 min at 4, 12 or 30° C.

Results of this experiment are depicted in Table 9. Some variants have very low activity at reduced temperature, suggesting that any proteolytic activity during cheese ripening will be very low. Especially variant 95 stands out since proteolytic activity is virtually absent at 4 and 12° C.

TABLE 9

Proteolytic activity of chymosin variants measured at pH 5 and different temperatures

| Temperature | 4 | 12 | 32 |
|---|---|---|---|
| Maxiren | 0.70 | 0.81 | 1.03 |
| Chymax M | 0.33 | 0.39 | 0.54 |
| 46 | 0.20 | 0.22 | 0.34 |
| 71 | 0.40 | 0.53 | 0.66 |
| 74 | 0.17 | 0.21 | 0.31 |
| 80 | 0.10 | 0.17 | 0.49 |
| 89 | 0.14 | 0.22 | 0.42 |
| 95 | 0.03 | 0.05 | 0.24 |
| 98 | 0.36 | 0.38 | 0.65 |
| 103 | 0.23 | 0.24 | 0.37 |
| 104 | 0.17 | 0.20 | 0.35 |
| 106 | 0.09 | 0.10 | 0.16 |
| 110 | 0.36 | 0.42 | 0.70 |

Example 9: Proteolytic Activity at Lower pH

Using the alternative proteolytic assay described in Example 8, we also examined the proteolytic activity at different pH. All incubations were at 30 degrees Celsius for 60 minutes and the pH of the substrate solution was adjusted to 5.0, 5.5, 6.0, 6.5 and 7.0 before the incubation. Results were normalized for the activities that were measured at pH 7.0 and plotted in Table 10. From this Table it becomes apparent that several variants show hardly stimulation of the proteolytic activity with decreased pH. Especially variants 71, 74, 95, 98, 103, 104 and 106 show a reduced stimulation of the proteolytic activity with lower pH compared to Maxiren and Chymax M. Variant 95 is special in that there is virtually no stimulation of the proteolytic activity when the pH is decreased until 5.0. Since the pH of most cheeses is lower than the milk pH, such a coagulant with reduced response to reduction of the pH can have profound effects on ripening of the cheese and is favorable for the production of cheeses where proteolysis leads to defects in processing.

TABLE 10

Relative proteolytic activity of different chymosin variants measured at different pH.

| pH | 5 | 5.5 | 6 | 6.5 | 7 |
|---|---|---|---|---|---|
| Maxiren | 2.6 | 2.4 | 2.2 | 1.6 | 1.0 |
| Chymax M | 3.7 | 3.4 | 3.2 | 1.7 | 1.0 |
| 71 | 1.7 | 1.5 | 1.2 | 1.1 | 1.0 |
| 74 | 2.0 | 1.8 | 1.6 | 1.2 | 1.0 |
| 95 | 1.2 | 1.3 | 1.1 | 1.0 | 1.0 |
| 98 | 2.2 | 2.0 | 1.7 | 1.3 | 1.0 |
| 103 | 2.1 | 2.0 | 1.7 | 1.1 | 1.0 |
| 104 | 2.4 | 2.1 | 1.8 | 1.3 | 1.0 |
| 106 | 1.8 | 2.0 | 1.4 | 1.4 | 1.0 |

The invention claimed is:

1. A polypeptide comprising an amino acid sequence having at least 90% identity to SEQ ID NO: 2, wherein the polypeptide has:
   chymosin activity;
   increased specificity, as compared to the polypeptide of SEQ ID NO: 2; and
   comprises at least one substitution corresponding to a substitution in the polypeptide of SEQ ID NO: 2 selected from A51I, A51L, A51N, A51T, and A51V.

2. The polypeptide of claim 1, wherein the polypeptide has decreased proteolysis in a cheese matrix and/or increased productivity as compared with the polypeptide of SEQ ID NO:2.

3. The polypeptide of claim 2, wherein the polypeptide has reduced curd targeting or reduced thermostability as compared with the polypeptide of SEQ ID NO:2.

4. The polypeptide of claim 2, further comprising at least one substitution at a position corresponding to a position in the polypeptide of SEQ ID NO: 2 selected from positions 48, 50, 61, 62, 109, 117, 126, 135, 144, 160, 161, 201, 202, 203, 221, 223, 240, 242, 244, 254, 267, 280, 292, and 295.

5. The polypeptide of claim 2, further comprising at least one substitution at a position corresponding to a position in the polypeptide of SEQ ID NO: 2 selected from positions 48, 50, 53, 109, 126, 135, 144, 160, 201, 221, 242, 267, and 280, and wherein the polypeptide has reduced temperature stability as compared with the polypeptide of SEQ ID NO: 2.

6. The polypeptide of claim 1, wherein the polypeptide has increased specific activity or increased expression level as compared with the polypeptide of SEQ ID NO:2.

7. The polypeptide of claim 6, further comprising at least one substitution at a position corresponding to a position in the polypeptide of SEQ ID NO: 2 selected from positions 98, 109, 112, 117, 126, 135, 144, 161, 202, 203, 221, 223, 240, 244, 254, 273, and 295, and wherein the polypeptide has increased specific activity as compared with the polypeptide of SEQ ID NO: 2.

8. The polypeptide of claim 6, further comprising at least one substitution at a position corresponding to a position in the polypeptide of SEQ ID NO: 2 selected from positions 50, 53, 109, 135, 144, 160, 201, 242, 267, 280, and 295, and wherein the polypeptide has an increased expression level as compared with the polypeptide of SEQ ID NO: 2.

9. The polypeptide of claim 1, further comprising at least one substitution at a position corresponding to a position in the polypeptide of SEQ ID NO: 2 selected from positions 2, 22, 40, 76, 88, 98, 99, 112, 125, 144, 163, 187, 189, 194, 200, 223, 271, 278, 284, 289 and 294, and wherein the polypeptide has decreased specificity as compared with the polypeptide of SEQ ID NO: 2.

10. The polypeptide of claim 1, further comprising at least one substitution at a position corresponding to a position in the polypeptide of SEQ ID NO: 2 selected from positions 48, 50, 53, 144, 160, 201, 242, 267, and 280, and wherein the polypeptide has increased clotting activity at low pH as compared with the polypeptide of SEQ ID NO: 2.

11. The polypeptide of claim 1, further comprising at least one substitution at a position corresponding to a position in the polypeptide of SEQ ID NO: 2 selected from positions 126, 135, and 221, and wherein the polypeptide has decreased proteolytic activity at low pH as compared with the polypeptide of SEQ ID NO: 2.

12. The polypeptide of claim 1, further comprising at least one substitution at a position corresponding to a position in the polypeptide of SEQ ID NO: 2 selected from positions 109, 126, 135, and 221, and wherein the polypeptide has decreased proteolytic activity at low temperature as compared with the polypeptide of SEQ ID NO: 2.

13. The polypeptide of claim 1, wherein said polypeptide comprises substitutions corresponding to substitutions in the polypeptide of SEQ ID NO: 2 selected from the group consisting of:
   A51I and K221I;
   A51I and K221T;
   A51I, K221I, S135T, and A126G;
   A51I, K221T, S135T, and A126G;
   A51L;
   A51N;
   A51T and K221T;
   A51T, K221T, S135T, and A126G;
   A51T;
   A51V and K221M;
   A51V and K295Q;
   A51V, N50D, K53Q, N144H, N160D, S201D, Q242E, M267E, and Q280E;
   A51V, E109Q, and K221M;
   A51V, K221L, and V223F;
   A51V, K221L, and K295Q;
   A51V, K221M, and V223F;
   A51V, K221M, and K295Q;
   A51V, K221V, N50D, K53Q, N144H, N160D, S201D, Q242E, M267E, and Q280E;
   A51V, K221V, N50D, N144H, N160D, S201D, Q242E, M267E, and Q280E;
   A51V, K221V, S135T, and A126G;
   A51V, K221V, S135T, A126G, and E109Q;
   A51V, K221V, S135T, A126G, and Q240E;
   A51V, K221V, S135T, A126G, and S273Y;
   A51V, K221V, S135T, A126G, S273Y, and Q240E;
   A51V, K221V, S135T, A126G, and K295Q;
   A51V, K221V, and V223F; and
   A51V, K221V, and K295Q.

14. The polypeptide of claim 1 having at least 95% sequence identity with the polypeptide of SEQ ID NO: 2.

15. A composition comprising the variant polypeptide according to claim 1.

16. The polypeptide of claim 1 capable of being used in preparation of a cheese.

17. A process for preparing cheese, wherein said method comprises clotting milk by adding an effective amount of the polypeptide of claim 1 to milk and further processing the clotted milk to manufacture cheese.

* * * * *

SEQUENCE LISTING

```
<160> NUMBER OF SEQ ID NOS: 2

<210> SEQ ID NO 1
<211> LENGTH: 1119
<212> TYPE: DNA
<213> ORGANISM: Bos taurus

<400> SEQUENCE: 1
ctcgagaaaa gagctgaaat caccagaatt ccattgtaca agggtaagtc tttgagaaag      60
gctttgaagg aacacggtct attggaagat ttcttacaaa agcaacagta cggtattct      120 tccaagtact ccggtttcgg tgaagttgcc tccgtcccat tgaccaacta tctggactct     180
caatatttcg gtaagatcta cttgggtact ccacctcaag agttcaccgt ccttttcgac     240
actggttctt ctgatttctg ggttccatcc atctactgta agtccaatgc ttgtaagaac     300
catcaaagat ttgacccaag aaagtcttcc actttccaaa acttgggtaa gccattatcc     360
attcactatg gtactggttc catgcaaggt atcttggggt acgacactgt tactgtttcc     420
aacattgttg acattcaaca aaccgtcggt ttgtccactc aagagcctgg cgatgttttc     480
acctacgctg aatttgatgg tattttgggt atggcttacc catctttggc ttctgaatac     540
tccatccctg tcttttgacaa catgatgaac cgtcacttgg ttgctcaaga tttattctcc     600
gtttacatgg acagaaacgg tcaagaatcc atgttgactt taggtgccat tgatccatct     660
tactacactg gttctctaca ctgggttcca gttaccgtcc aacaatactg gcaattcacc     720
gttgactccg tcaccatctc cggtgttgtt gttgcttgtg aaggtggttg ccaagctatc     780
```

-continued

```
ttggacaccg gtacttccaa gttggtcggt ccatcttctg atatcttgaa cattcaacaa      840
gccattggtg ccactcaaaa ccagtacggt gaattcgata ttgactgtga caacttgtct      900
tacatgccaa ctgttgtctt tgaaatcaat ggtaagatgt acccattaac cccatctgct      960
tacacttctc aagaccaagg tttctgtact tctggtttcc aatctgaaaa ccattctcaa     1020
aaatggatct tgggtgatgt cttcatcaga gagtactact ccgtctttga ccgtgccaac     1080
aacttggttg gtttggccaa ggccatctaa gttaattaa                            1119
```

<210> SEQ ID NO 2
<211> LENGTH: 323
<212> TYPE: PRT
<213> ORGANISM: Bos taurus

<400> SEQUENCE: 2

```
Gly Glu Val Ala Ser Val Pro Leu Thr Asn Tyr Leu Asp Ser Gln Tyr
  1               5                  10                  15

Phe Gly Lys Ile Tyr Leu Gly Thr Pro Pro Gln Glu Phe Thr Val Leu
                 20                  25                  30

Phe Asp Thr Gly Ser Ser Asp Phe Trp Val Pro Ser Ile Tyr Cys Lys
             35                  40                  45

Ser Asn Ala Cys Lys Asn His Gln Arg Phe Asp Pro Arg Lys Ser Ser
         50                  55                  60

Thr Phe Gln Asn Leu Gly Lys Pro Leu Ser Ile His Tyr Gly Thr Gly
 65                  70                  75                  80

Ser Met Gln Gly Ile Leu Gly Tyr Asp Thr Val Thr Val Ser Asn Ile
                 85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
        115                 120                 125

Ser Leu Ala Ser Glu Tyr Ser Ile Pro Val Phe Asp Asn Met Met Asn
    130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

Phe Thr Val Asp Ser Val Thr Ile Ser Gly Val Val Ala Cys Glu
        195                 200                 205

Gly Gly Cys Gln Ala Ile Leu Asp Thr Gly Thr Ser Lys Leu Val Gly
    210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Phe Glu Ile Asn Gly Lys Met Tyr Pro Leu Thr Pro
            260                 265                 270

Ser Ala Tyr Thr Ser Gln Asp Gln Gly Phe Cys Thr Ser Gly Phe Gln
        275                 280                 285

Ser Glu Asn His Ser Gln Lys Trp Ile Leu Gly Asp Val Phe Ile Arg
    290                 295                 300
```

```
Glu Tyr Tyr Ser Val Phe Asp Arg Ala Asn Asn Leu Val Gly Leu Ala
305                 310                 315                 320

Lys Ala Ile
```